(12) United States Patent
Gerold

(10) Patent No.: US 8,268,235 B2
(45) Date of Patent: Sep. 18, 2012

(54) IMPLANT WITH A BASE BODY OF A BIOCORRODIBLE MAGNESIUM ALLOY

(75) Inventor: Bodo Gerold, Zellingen (DE)

(73) Assignee: Biotronik VI Patent AG, Baar (CH)

( * ) Notice: Subject to any disclaimer, the term of this patent is extended or adjusted under 35 U.S.C. 154(b) by 248 days.

(21) Appl. No.: 12/640,687

(22) Filed: Dec. 17, 2009

(65) Prior Publication Data

US 2010/0198332 A1 Aug. 5, 2010

(30) Foreign Application Priority Data

Jan. 30, 2009 (EP) .................................... 09151691

(51) Int. Cl.
*C22C 23/00* (2006.01)
*C22C 23/04* (2006.01)
*C22C 23/06* (2006.01)

(52) U.S. Cl. ........ 420/406; 420/402; 420/405; 420/411; 420/414; 148/420; 148/666; 148/667; 424/423; 623/1.15; 623/1.42

(58) Field of Classification Search .................. 420/402, 420/405, 406, 411, 414; 148/420, 666, 667; 424/423; 623/1.15, 1.42
See application file for complete search history.

(56) References Cited

U.S. PATENT DOCUMENTS

| 3,370,945 A * | 2/1968 | Foerster et al. ................ 420/410 |
| 2002/0004060 A1 | 1/2002 | Heublein et al. |
| 2004/0098108 A1 | 5/2004 | Harder et al. |
| 2004/0241036 A1 | 12/2004 | Meyer-Lindenberg et al. |
| 2006/0228249 A1 * | 10/2006 | Lyon et al. ..................... 420/406 |
| 2009/0171452 A1 * | 7/2009 | Yamamoto et al. .......... 623/1.38 |
| 2010/0161031 A1 * | 6/2010 | Papirov et al. ............... 623/1.15 |
| 2011/0229365 A1 * | 9/2011 | Lyon et al. ..................... 420/406 |

FOREIGN PATENT DOCUMENTS

| DE | 197 31 021 | 1/1999 |
| EP | 1 419 793 | 5/2004 |
| EP | 1 632 256 | 3/2006 |
| EP | 1 842 507 | 10/2007 |
| WO | WO 2005/044175 | 5/2005 |
| WO | WO 2007/107286 | 9/2007 |
| WO | WO 2008/145244 | 12/2008 |

OTHER PUBLICATIONS

Machine-English translation of European patent 1632256 A2, Harder Claus et al., Mar. 8, 2006.*
Machine-English translation of Chinese patent 1676646 A, Ding Wenjiang et al., Oct. 5, 2005.*
European Patent Office, Search Report for Priority European Application No. 09151691.4, Issued Jun. 10, 2009.
Nicolosi Alfred C. et al., Abstract of "Gadolinium attenuates regional stunning in the canine heart in vivo," Database Medline, U.S. National Library of Medicine (NLM), Bethesda, MD, US; Jul. 2002; XP002529907; The Journal of Thoracic and Cardiovascular Surgery.

* cited by examiner

*Primary Examiner* — Deborah Yee
(74) *Attorney, Agent, or Firm* — Greer, Burns & Crain, Ltd.

(57) ABSTRACT

An implant consisting entirely or in part of a biocorrodible magnesium alloy having the composition
Gd: 2.7-15.0 wt %,
Zn: 0-0.5 wt %,
Zr: 0.2-1.0 wt %,
Nd: 0-4.5 wt %,
Y: 0-2.0 wt %,
where magnesium and impurities due to the production process account for the remainder to a total of 100 wt %.

19 Claims, 5 Drawing Sheets

A) DF9425

B) DF9267

C) DF9403

D) DF9521

IMPLANT WITH A BASE BODY OF A BIOCORRODIBLE MAGNESIUM ALLOY

CROSS REFERENCE

This application claims the benefit of European Application No. 09151691.4, filed Jan. 30, 2009 which is incorporated by reference herein.

FIELD OF THE INVENTION

The invention relates to an implant with a base body consisting entirely or in part of a biocorrodible magnesium alloy.

TECHNOLOGICAL BACKGROUND AND STATE OF THE ART

Implants are used in modern medical technology in a variety of embodiments. They serve to support blood vessels, hollow organs and duct systems (endovascular implants), to fasten and temporarily secure tissue implants and tissue transplants, but also for orthopedic purposes, e.g., as nails, plates or screws, among other things.

Implantation of stents is one of the most effective therapeutic measures in treatment of vascular diseases. The purpose of stents is to assume a supporting function in a patient's hollow organs. Stents of a traditional design therefore have a filigree supporting structure comprising metallic struts, which are initially in a contracted form for introducing them into the body and are widened at the site of application. One of the main areas of application of such stents is for permanently or temporarily widening vascular constrictions and keeping them open, in particular stenoses of coronary vessels. In addition, aneurysm stents are also known for supporting damaged vascular walls.

The base body of each implant, in particular of a stent, comprises an implant material. An implant material is a nonviable material that interacts with biological systems and is used for administration in medicine. The basic prerequisites for using a material as an implant material, which comes in contact with the physical environment when used as intended, is its physical compatibility (biocompatibility). Biocompatibility is understood to be the ability of a material to induce a suitable tissue reaction in a specific application. This includes adaptation of the chemical, physical, biological and morphological surface properties of an implant to the recipient tissue with the goal of achieving a clinically desired interaction. The biocompatibility of an implant material also depends on the reaction of the biosystem in which it is implanted over time. For example, irritation and inflammation occur in a relatively short period of time and may lead to tissue changes. Biological systems thus react in different ways, depending on the properties of the implant material. According to the reaction of the biosystem, implant materials can be subdivided into bioactive, bioinert and degradable/absorbable materials. For the purposes of the present invention, only degradable/absorbable metallic implant materials, which are referred to below as biocorrodible metallic materials, are of interest.

The use of biocorrodible metallic materials is recommended in particular because an implant must often remain only temporarily in the body to fulfill the medical purpose. Implants of permanent materials, i.e., materials that do not degrade in the body, may have to be removed again because rejection reactions in the body may occur in the medium range and long range, even when there is a high biocompatibility.

One approach to prevent an additional surgical procedure thus consists of making the implant entirely or in part of a biocorrodible metallic material. Biocorrosion is understood to refer to processes which are caused by the presence of endogenous media and lead to a gradual degradation of the structure of which the material is comprised. At a certain point in time, the implant or at least the part of the implant made of the biocorrodible material, loses its mechanical integrity. The degradation products are mostly absorbed by the body. As in the case of magnesium, for example, in the best case the degradation products even have a positive therapeutic effect on the surrounding tissue. Small quantities of unabsorbed alloy ingredients can be tolerated.

Known biocorrodible metallic materials include pure iron and biocorrodible alloys of the main elements magnesium, iron, zinc, molybdenum and tungsten. DE 197 31 021 A1 proposes that medical implants should be made of a metallic material whose main ingredient is an element from the group of alkali metals, alkaline earth metals, iron, zinc and aluminum. Alloys based on magnesium, iron and zinc are described as being especially suitable. Secondary constituents of the alloys may be manganese, cobalt, nickel, chromium, copper, cadmium, lead, tin, thorium, zirconium, silver, gold, palladium, platinum, silicon, calcium, lithium, aluminum, zinc and iron.

EP 1 419 793 B1 describes the use of a biocorrodible magnesium alloy containing >90 wt % magnesium, 3.7-5.5 wt % yttrium, 1.5-4.4 wt % rare earth metals and the remainder <1 wt % to produce a stent.

EP 1 842 507 A1 describes an implant of a base body consisting of an yttrium-free and gadolinium-containing magnesium alloy. The alloy may also contain neodymium (Nd), zinc (Zn), zirconium (Zr) and calcium (Ca). The alloy preferably contains 1.0 to 5.0 wt % Gd and 1.0 to 5.0 wt % Nd to keep the cytotoxicity at a low level and to improve the mechanical properties such as strength, hardness and ductility as well as the processability of the material. The Zn and Zr content preferably amount to 0.1 to 3.0 wt % each to ensure a homogeneous distribution of the elements in the alloy.

Biodegradable vascular supports (stents) made of magnesium alloys have already been tested in clinical studies. A magnesium alloy containing yttrium and rare earths, technical designation WE43, has been used. When using this alloy, which has already been tested in other areas of implantology in animal experiments, some properties still pose problems in a physiological environment. Specifically, these WE alloys have a tendency to degrade rapidly in physiological media, trigger an excessive release of degradation products into the surrounding tissue and an excessive release of hydrogen at the site of implantation. In addition, these alloys manifest unwanted reactions in the process of manufacturing the implants. It has been found that repeated thermomechanical shaping processes in the production of precursors—for example, in manufacturing tubes for the production of stents by tube drawing or by extrusion—can significantly impair the processability and the mechanical properties of the material.

SUMMARY OF THE INVENTION

The feature of the present invention is to solve or at least ameliorate one or more of the problems described above. In particular, an implant made of a biocorrodible magnesium alloy that has been improved with regard to its corrosion behavior and mechanical properties is to be made available. If possible, the processability of the implant material is also to be improved. Finally, toxicological aspects pertaining to the tissue environment are also to be taken into account.

The inventive implant solves or improves one or more of the features described above. The invention is directed to an implant comprising entirely or in part a biocorrodible magnesium alloy.

The magnesium alloy has the composition
Gd: 2.7-15.0 wt %,
Zn: 0-0.5 wt %,
Zr: 0.2-1.0 wt %,
Nd: 0-4.5 wt %,
Y: 0-2.0 wt %,
where magnesium plus the impurities due to the manufacturing process account for the remainder up to a total of 100 wt %.

The invention is based on the finding that the degradation tendency can be reduced, the mechanical properties can be improved and problems in processing the implant material can be reduced by using the inventive biocorrodible magnesium alloy.

The alloy contains no yttrium or up to max. 2 wt % yttrium. Although yttrium has the effect of promoting strength and increasing corrosion resistance by forming yttrium oxides on the surface, it also tends to form precipitations having a very high thermal stability, especially in interaction with neodymium, and to make it difficult—or in the worst case even impossible—to process the material in a manner that preserves the mechanical properties. In the melt, Y reduces burn-off of the other rare earths and thus facilitates production. The amount of Y in the alloy is therefore preferably 0.05 to 0.5 wt %.

Except for Gd, Nd and optionally Y, the alloy is free of other rare earths in addition to the alloy constituents. The other rare earths, e.g., lanthanum have a very low solubility in magnesium. Due to their low solubility, these elements form intermetallic phases, so-called precipitations. These elements are also characterized in that they have a very low diffusion rate and participate in the formation of precipitations having a very high thermal stability. They thus make a significant contribution to the mechanical properties of Mg alloys at high temperatures. On the other hand properties can also deteriorate, especially at room temperature, when the particles are too large.

On the other hand, however, such precipitations form a problem for biomedical use, e.g., as a stent, where they massively interfere with the thermomechanical processability of the alloy. Therefore, in most cases drawn tubes are preferably used for processing to stents today. In the course of production of such tubes by drawing or extrusion, the material is repeatedly exposed to cycles of high mechanical deformation and subsequent heat treatments.

In mechanical deformation, the intermetallic phases of the rare earths except for Gd and Y are problematical because they also have a much higher hardness than the surrounding matrix material. As a result, the particles are ground off. This may result in separation of material (cracking) or formation of defects in the material. Such defects may then heal only incompletely as a result of welding during forming or in the subsequent heat treatment. The processability of the material is thus definitely limited and the properties of the material become progressively worse in thermomechanical processing. Implants, especially stents, produced from this material have inferior mechanical properties accordingly.

In comparison with the prior art, the inventive alloy system is characterized in that complete or almost complete dissolution of all the precipitated intermetallic phases is achieved by heat treatment. The required plastic deformability of the material and the desired mechanical properties of the material are thus preserved over the entire manufacturing process. It has been found that due to the great increase in the Gd content—with the same Nd content, however, in comparison with conventional WE alloys—the strength of the alloy can be increased without having to accept the negative influences on the processability of the material as described above.

The inventive alloy exhibits improved mechanical properties. It has an increased strength, i.e., the range between the onset of plastic deformation and reaching the tensile strength and/or compressive strength is optimized according to the uniform elongation. The elongation range is large and shows a uniform increase in the stress, strength and deformability required for further deformation. If the implant is a stent, the material allows an improvement in the supporting force and the diameter of the struts in the stent can be kept small.

It has additionally been found that the alloys used according to this invention have a reduced corrosion tendency in a physiological environment. The corrosion-inhibiting effect is associated with the fact that more Gd is dissolved in the matrix. In addition, the amount by volume of Gd-containing intermetallic phases (precipitations) (approximately 6% with 1.32 wt % Gd to 30% with 15 wt % Gd), which also increases with an increase in Gd content, surprisingly appears not only not to have a negative effect on corrosion resistance but, if possible, even has a positive effect, contrary to the prevailing opinion and observations with other rare earths. Intermetallic phases actually form local elements which lead to increased dissolution of the matrix around the particles because they are usually much more noble, when considered from an electrochemical standpoint.

The metal ions released in the in-vivo degradation of the inventive alloy evidently also have a positive pharmacological effect on the surrounding tissue, according to preliminary experiments, in particular in the case of a stent used as intended. This positive effect seems to be attributable to a high concentration of free gadolinium ions. However, free Gd is a very short-lived form of the element and undergoes phagocytosis by immunological cells as Gd hydroxide or Gd phosphate. It is known that free gadolinium ions behave like calcium ions, i.e., they are incorporated mainly in the liver and in the bone system, where they may remain for many years. Free gadolinium as a calcium antagonist (the ionic radii of calcium and gadolinium are almost identical) also influences the myocardial contractility and inhibits the coagulation system. Free gadolinium ions administered intravenously in a dose of 0.1 mmol/kg solution have an acute toxicity. The smooth muscles and the transverse striated muscles, the function of the mitochondria and blood coagulation are affected by this toxicity. It has now been demonstrated that, contrary to the theory, Mg alloys having a high Gd content lead to reduced vascular contraction, inhibit neointima proliferation and slow the in-vivo degradation of the material through reduced macrophage activity. The vasodilating influence of a high Gd content in conjunction with biodegradable magnesium alloys is of special importance because some of the degradation products are suspected of triggering vasocontraction, which could damage the stent and reduce the vascular volume again. This effect can be counteracted by simultaneous release of Gd. Therefore, another aspect of the present invention is to provide a biocorrodible alloy, preferably magnesium alloys of the compositions given above, containing 5.1 to 15.0 wt % Gd as a means for prevention of restenosis or as a vasodilating drug (vasodilator).

The composition of the magnesium alloy is to be selected so that it is biocorrodible. Artificial plasma such as that specified according to EN ISO 10993-15:2000 for biocorrosion tests (composition NaCl 6.8 g/L, $CaCl_2$ 0.2 g/L, KCl 0.4 g/L, $MgSO_4$ 0.1 g/L, $NaHCO_3$ 2.2 g/L, $Na_2HPO_4$ 0.126 g/L, $NaH_2PO_4$ 0.026 g/L) is used as the test medium for testing the corrosion behavior of alloys. A sample of the material to be investigated is then stored in a sealed sample container with a defined amount of the test medium at 37° C. At intervals of a few hours up to several months (based on the expected corrosion behavior), the samples are removed and examined for signs of corrosion by known methods. The artificial plasma according to EN ISO 10993-15:2000 corresponds to a blood-like medium and thus constitutes a possibility for reproducibly simulating a physiological environment in the sense of the present invention.

The inventive biocorrodible magnesium alloys can be produced and processed according to the procedures for manufacturing known magnesium alloys. Extremely pure starting materials ($\geqq$99.9%) are usually melted under a blanket of protective gas and are then shaped to semifinished products by casting, rolling, drawing or extrusion.

An amount of Gd in the alloy preferably amounts to 7.0 to 13.0 wt %. The pharmacological effects of the Gd ions released on degradation of the material in the body can thus be ensured in particular.

It has been found that addition of Zn increases the corrosion resistance of the alloy. An amount of Zn in the alloy preferably is 0.1-0.5 wt %, in particular 0.15 to 0.25 wt %.

Furthermore, it has been found that the addition of 0.2-1.0 wt % Zr greatly improves the corrosion properties, presumably due to the binding of impurities such as iron. An amount of Zr in the alloy is preferably 0.2 to 0.7 wt %.

The Nd content of the alloy preferably amounts to 1.5 to 4.5 wt %, in particular 2.0 to 3.0 wt %, especially preferably 2.0-2.5 wt %. In this way, the processability of the alloy can be promoted by casting and kneading. The mechanical properties such as the strength of the alloy are also determined to a significant extent by Nd. If the Nd content amounts to at least 1.5 wt %, then the strength of the alloy is improved. If the Nd content exceeds 4.5 wt %, then the ductility of the alloy is worsened because of the limited solubility of Nd.

Table 1 shows the solubilities of various rare earths in magnesium at temperatures of 200° C., 400° C. and 500° C. From this information, one might expect the volume of the coarse-grained particles to correlate directly with the Nd content because this element has a low solubility, and a high Gd content should further reduce the solubility limit. It has surprisingly now been found that omitting rare earths except for the aforementioned Nd and Gd in the alloy has a substantial effect on the distribution, appearance and composition of intermetallic phases and in particular significantly reduces the volume of the Nd-rich particles which can be explained by the effect that Nd possibly reduces the solubility of Gd in magnesium.

TABLE 1

| | | Solubility (wt %) | | |
|---|---|---|---|---|
| Ordinal number | Element | 200° C. | 400° C. | 500° C. |
| 68 | Er | 16 | 23 | 28 |
| 66 | Dy | 10 | 17.8 | 22.5 |
| 64 | Gd | 3.8 | 11.5 | 19.2 |
| 70 | Yb | 2.5 | 4.8 | 8 |
| 62 | Sm | 0.4 | 1.8 | 4.3 |
| 58 | Ce | 0.04 | 0.08 | 0.26 |
| 59 | Pr | 0.01 | 0.2 | 0.6 |
| 60 | Nd | 0.08 | 0.7 | 2.2 |
| 57 | La | — | 0.01 | 0.03 |

Impurities due to Pr, which is a contaminant of Gd, from the production process may be tolerated up to an amount of <0.2 wt %. The same thing is true of La.

In the sense of this invention, implants are devices introduced into the body by a surgical method or a minimally invasive method and comprise fastening elements for bones, e.g., screws, plates or nails, surgical suture material, intestinal clamps, vascular clips, prostheses in the area of soft and hard tissue, e.g., stents and anchoring elements for electrodes, in particular of pacemakers or defibrillators. The implant consists entirely or in part of the biocorrodible material.

The implant is preferably a stent. Stents of a traditional design have a filigree structure of metallic struts which are initially introduced into the body in a contracted state and are then expanded at the site of application into an expanded state.

DESCRIPTION OF THE DRAWINGS

The invention is explained in greater detail below on the basis of exemplary embodiments and the respective drawings, in which.

DETAILED DESCRIPTION ON THE BASIS OF EXEMPLARY EMBODIMENTS

To characterize the inventive alloy system, numerous compositions were melted, cast and extruded, and their microstructure, thermomechanical properties, corrosion behavior and physiological effects were determined with the help of different test methods.

General Procedure for Production of Alloy

High-purity starting materials ($\geqq$99.99%) were melted in steel crucibles under a protective gas ($CO_2$/2% $SF_6$). The temperature was raised to 760° C. to 800° C. before the melt was homogenized by stirring. The melt was cast to form bars with a diameter of 120 mm and a length of 300 mm. Next the bars were machined to a nominal diameter of 75 mm with a length of 150 mm to 250 mm and tempered for 4-8 hours at approximately 525° C.

The material was then extruded with the help of a hydraulic press and the resulting round rods had a diameter of 3.2 mm to 25 mm, mostly 9.5 mm. For the following investigations, end pieces 30 cm long were usually removed.

Table 1 summarizes the compositions of some comparative alloys and inventive alloy systems.

TABLE 2

| | Amount (wt %) | | | | | | | | |
|---|---|---|---|---|---|---|---|---|---|
| ID | Y | Nd | Zr | Gd | La | Ce | Pr | Fe | Zn |
| SF2894 | 3.74 | 2.15 | 0.52 | 0.15 | 0.06 | 0.01 | 0.00 | 0.003 | 0.00 |
| SF4619 | 3.90 | 2.20 | 0.56 | 0.28 | 0.00 | 0.00 | 0.00 | 0.002 | 0.00 |
| SF4355 | 3.90 | 2.10 | 0.51 | 0.34 | 0.00 | 0.00 | 0.00 | 0.003 | 0.00 |
| DF9085 | 0.00 | 2.70 | 0.38 | 1.42 | 0.01 | 0.05 | 0.09 | 0.003 | 0.23 |
| DF9425 | 0.00 | 2.80 | 0.42 | 1.32 | 0.00 | 0.04 | 0.08 | 0.002 | 0.30 |
| DF9267 | 0.00 | 2.50 | 0.32 | 6.00 | 0.01 | 0.08 | 0.15 | 0.002 | 0.22 |
| DF9087 | 0.10 | 2.30 | 0.31 | 7.50 | 0.01 | 0.07 | 0.07 | 0.003 | 0.01 |
| DF9263 | 0.10 | 2.10 | 0.30 | 6.69 | 0.00 | 0.00 | 0.00 | 0.002 | 0.00 |
| DF9403 | 0.00 | 2.60 | 0.35 | 8.04 | 0.01 | 0.09 | 0.14 | 0.002 | 0.24 |
| DF9521 | 0.00 | 3.00 | 0.40 | 15.0 | 0.01 | 0.14 | 0.19 | 0.003 | 0.21 |

Mechanical Properties and Metallurgical Description of the Alloy

Figure 1:
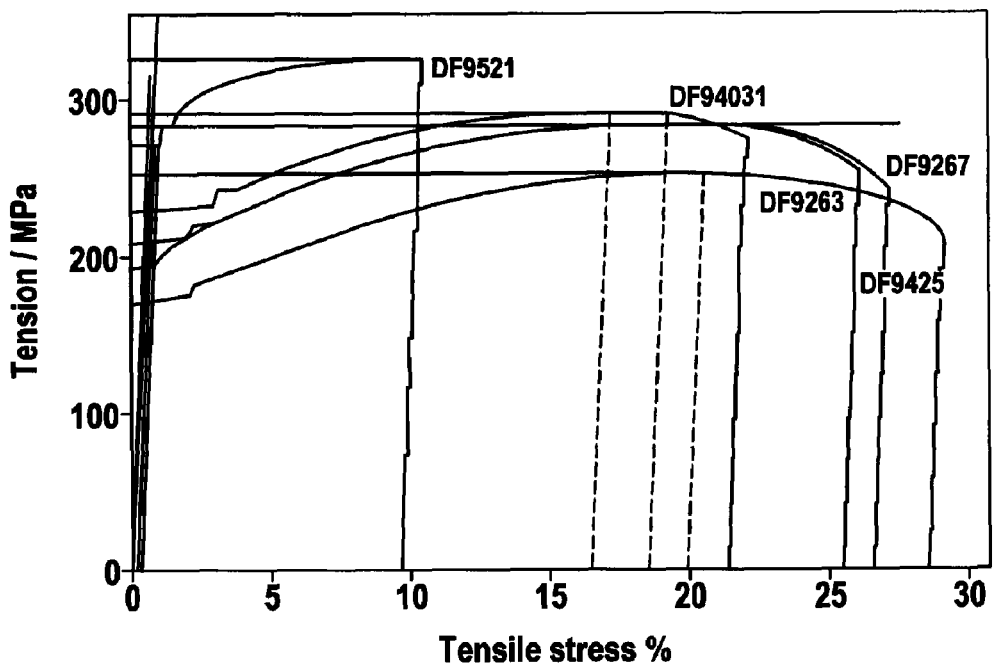
FIGS. 1 and 2 show tensile stress properties of selected alloy systems.

To determine the mechanical properties, standardized tension tests were performed and analyzed using several samples of a melt in each case. The 0.2% yield point (Rp 0.2%), the tensile strength (Rm), the uniform elongation (Ag) and elongation at break (A) were determined as characteristic data (FIG. 1).

Figure 2:
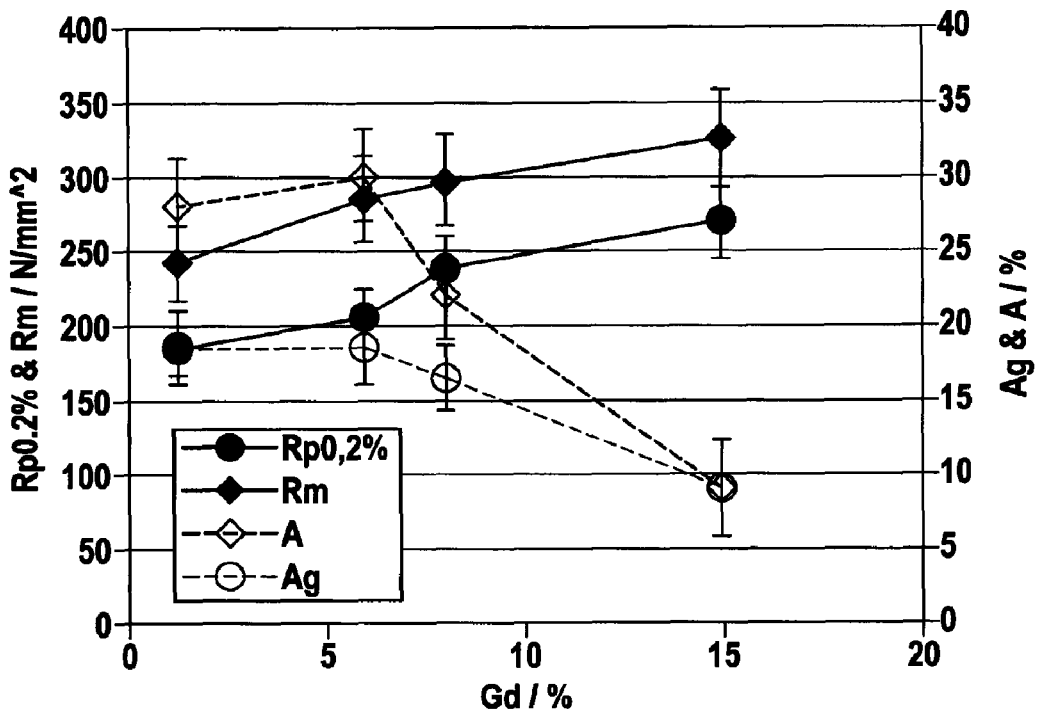

Table 3 shows the corresponding data for the alloy systems tested. As shown in FIG. 2, amounts of up to 15 wt % Gd lead to a continuous increase in the mechanical strength, which can be read in the values for the yield point and tensile strength. An increase in the Gd content above 8 wt % reduces the ductility of the material and leads to a significant reduction in the elongation at break. Surprisingly, the uniform elongation remains in a range that is large enough to ensure sufficient ductility for components such as stents which, above a Gd content of 8 wt %, are subject to high plastic stress. The data also show that the elongation at break begins to drop sharply above a Gd content of more than 8 wt %, but the uniform elongation turns out much lower.

TABLE 3

| ID | Rp0.2% (MPa) | Rm (MPa) | Ag (%) | A (%) |
|---|---|---|---|---|
| SF2894 | n/m | n/m | n/m | n/m |
| SF4619 | 209 | 298 | n/m | 19 |
| SF4355 | 218 | 286 | n/m | 19 |
| DF9085 | 155 | 234 | n/m | 31 |
| DF9425 | 183 | 242 | 20 | 29 |
| DF9267 | 205 | 285 | 18.5 | 26 |
| DF9087 | 205 | 289 | n/m | 27 |
| DF9263 | 211 | 283 | 18.5 | 25.5 |
| DF9403 | 238 | 296 | 16.5 | 21.5 |
| DF9521 | 269 | 325 | 9 | 9 |

Figure 8:
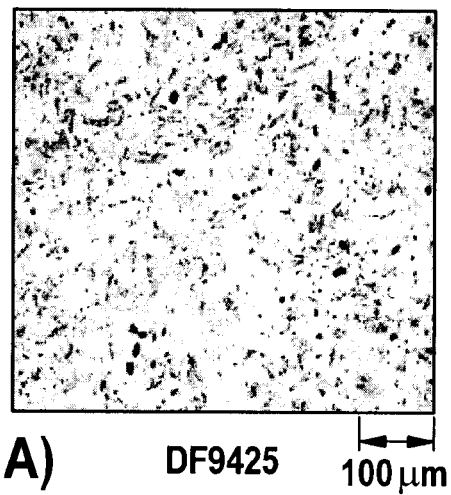
FIG. 8A)-D) show structural diagrams of alloys of inventive composition and/or traditional composition.
Figure 8:
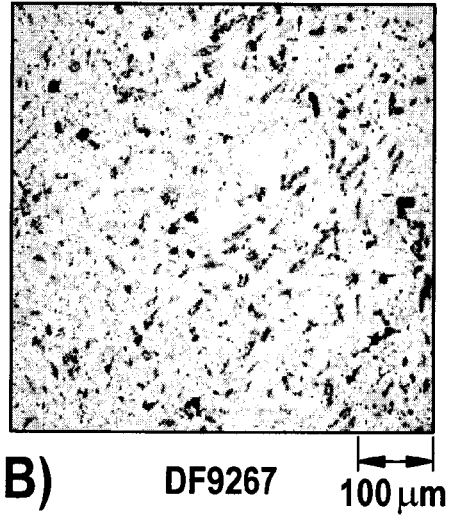
Figure 8:
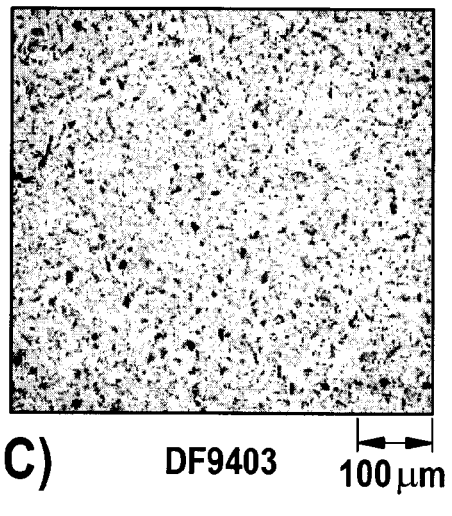
Figure 8:
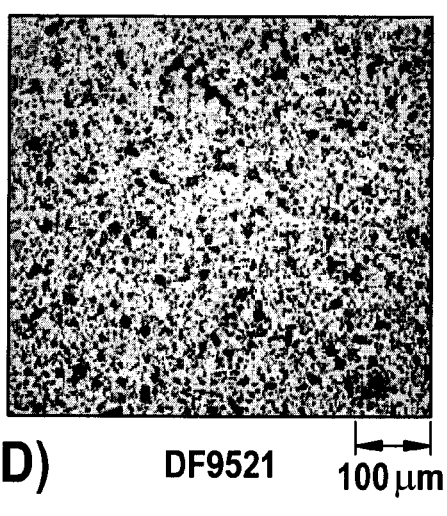

FIGS. 8A)-D) show clearly the structural images and in particular the volume ratios of the intermetallic phases of the inventive alloy B) DF9267 with a Gd content of 6 wt %, see DF9403 with approximately 8 wt % and D) DF9521 with 15 wt % in comparison with A) DF9425 with a Gd content of 1.32 wt %. The increasing amount by volume of Gd-containing intermetallic phases with an increase in Gd content is also apparent, from approximately 6 vol % at 1.32 wt % Gd to approximately 30 vol % at 15 wt % Gd.

Corrosion Behavior

The corrosion behavior of selected alloy systems was investigated in greater detail on the basis of three standardized tests. The results of these tests are summarized in Table 4.

First a standardized test to evaluate the industrial usability of the alloys was performed using a 5% NaCl-containing spray mist according to ASTM B117. The samples were exposed to the test conditions for 7 days and then the corrosion product was removed by boiling in a 10% chromium trioxide solution. The weight loss of the samples was determined and expressed in mpy (English: mils penetration per year) as is customary in international practice.

As FIG. 2 shows, the corrosion behavior and the salt spray mist was improved by a factor of approximately 2 in the alloy with 7-8 wt % Gd. A further increase in Gd content did not lead to any further improvement in the corrosion resistance under the aforementioned test conditions. Instead, the corrosion resistance even seems to be exacerbated.

However, the corrosion resistance also depends on the corrosion medium. Therefore, two additional test methods have been used to determine the corrosion behavior under physiological conditions in view of the special use of the alloys. These two test methods are based essentially on a determination of weight loss. In both methods, the samples are exposed to the corresponding physiological medium for a certain period of time and then the weight loss is determined.

In storage in PBS (phosphate buffered saline) small cylindrical samples of the extruded material are stored for 24 hours in a flowing hot medium at 37° C. with an ionic concentration of 354 mmol/L $Na^+$, 15 mmol/L $K^+$, 130 mmol/L $HPO_4^{2-}$ and 154 mmol/L $Cl^-$, and at various points in time the magnesium content of the medium is determined by ion chromatography.

For storage in SBF (simulated body fluid) with an ionic concentration of 142 mmol/L $Na^+$, 5 mmol/L $K^+$, 2.5 mmol/L $Ca^{2+}$, 1 mmol/l $Mg^{2+}$, 1 mmol/l $SO_4^{2-}$, 1 mmol/l $HPO_4^{2-}$, 109 mmol/l $Cl^-$ and 27 mmol/L $HCO_3^-$ cylindrical samples of the extruded material are used in accordance with ASTM B117. In contrast with the salt spray test, however, the samples are completely immersed in the hot medium for 7 days at 37° C. Then the corrosion product is removed by boiling in a 10% chromium trioxide solution. The weight loss of the samples was determined and expressed in mpy (English mils penetration per year), which is the international convention.

Figure 3:
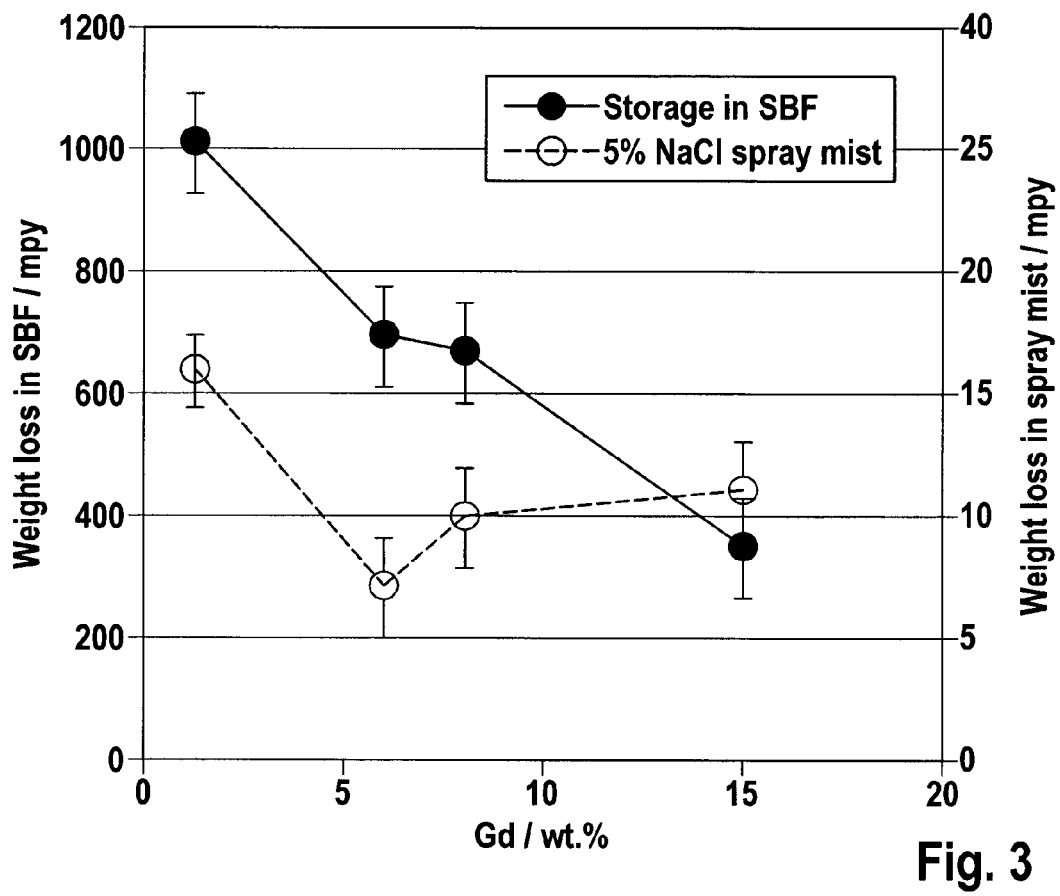
FIG. 3 shows a comparison of the weight loss of selected alloy systems in the NaCl spray mist test and SBF test.
Figure 4:
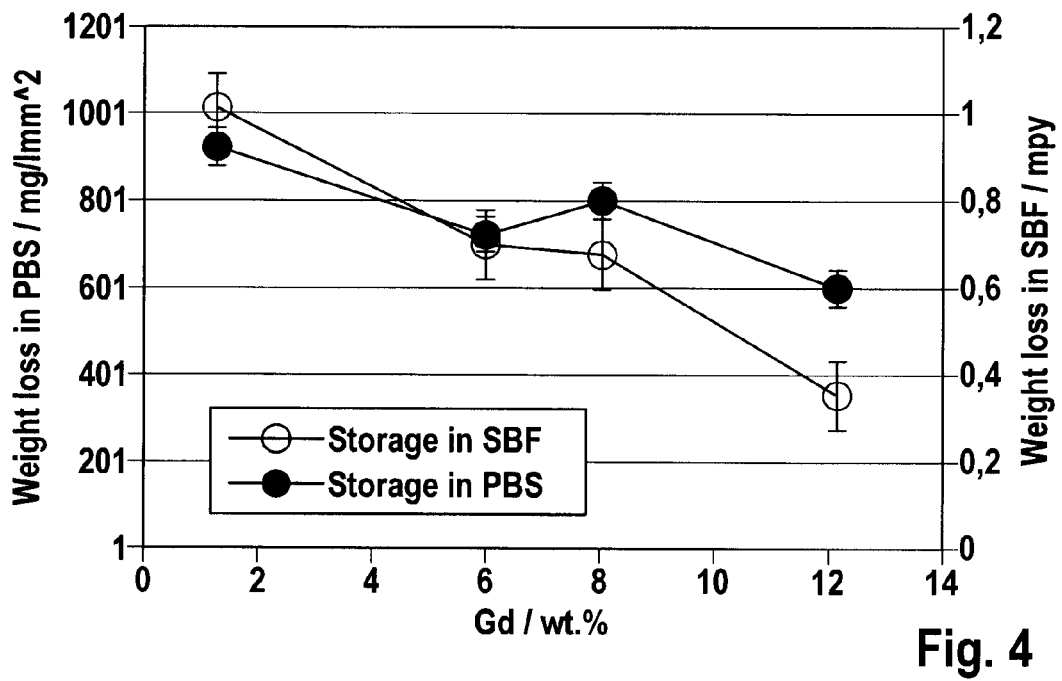
FIG. 4 shows a comparison of the weight loss of selected alloy systems in the SBF and PBS tests.

It has now been found that a continuous decline in weight loss under the test conditions is also associated with an increase in Gd content of up to 15 wt %. The results of these tests and the trends mentioned here are shown in Table 4 and FIGS. 3 and 4. The inventive alloy systems have thus surprisingly manifested a much better corrosion behavior in a physiological environment than was expected from the salt spray tests.

TABLE 4

| ID | 5% NaCl Test (mpy) | SBF Test (mpy) | PBS Test (mg/mm²) |
|---|---|---|---|
| SF2894 | 40 | | |
| SF4619 | 43 | | |
| DF9085 | 7 | n/m | n/m |
| DF9425 | 16 | 1011 | 0.92 |
| DF9267 | 7 | 697 | 0.72 |
| DF9087 | 44 | n/m | n/m |
| DF9263 | 25 | n/m | n/m |
| DF9403 | 9-12 | 671 | 0.8 |
| DF9521 | 11 | 353 | 0.6 |

In-vivo Tests

Figure 5:
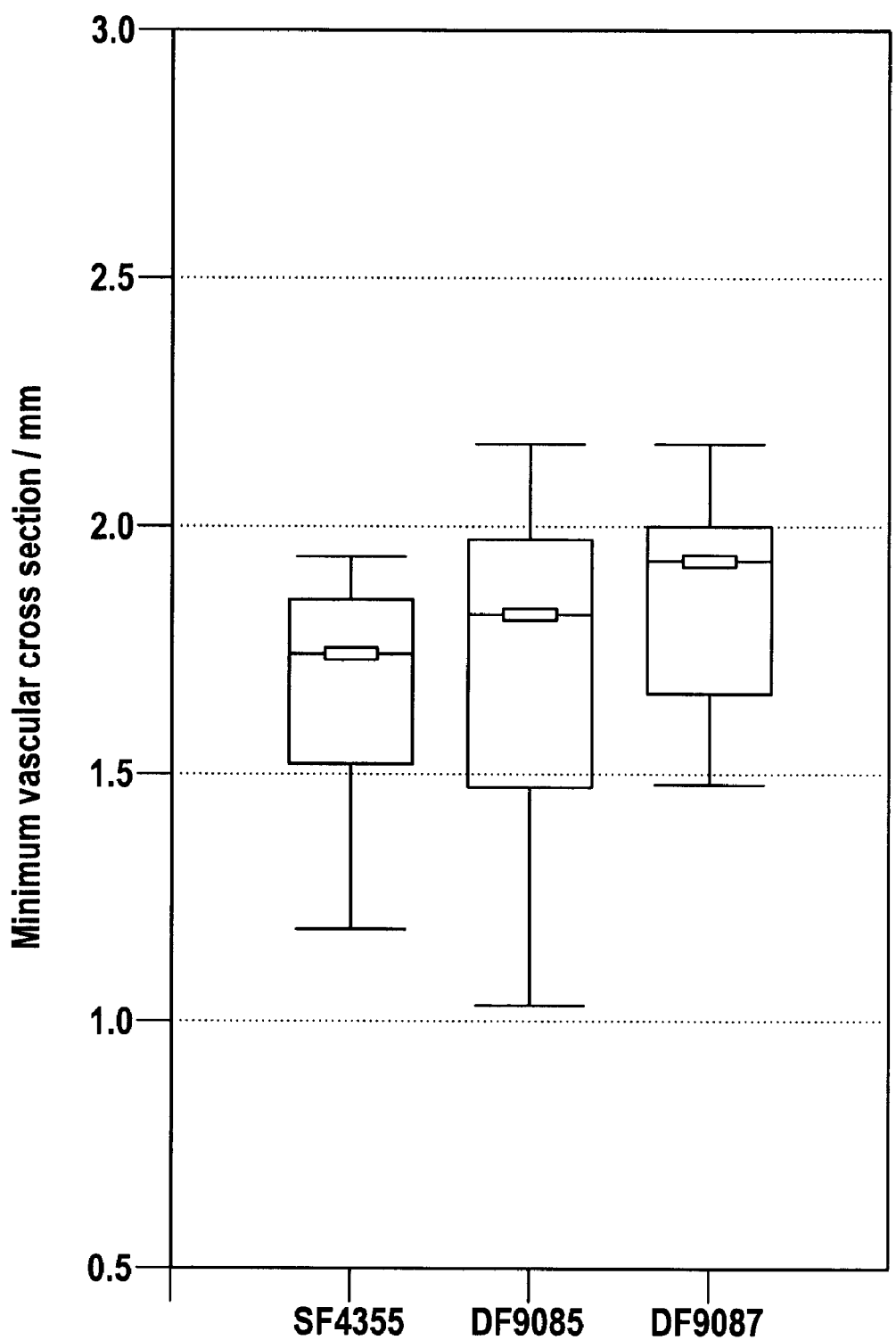
FIG. 5 shows a comparison of the lumen of dilated vessels with various alloy systems.

In-vitro tests are not always directly applicable to the conditions in a living organism. To determine the in-vivo performance, stents of various alloys were therefore tested in miniature pigs. One stent was implanted in each of the three major coronary arteries of each experimental animal. After 4 or 6 weeks, the arteries were explanted and subjected to morphometric and histological testing. Partial results of an initial study with DF9085 and DF9087 are shown in FIG. 5, which includes a comparison of the open vascular lumen of arteries with the different alloys tested. The alloy WE43 (SF4355) served as a reference.

As this shows, using an alloy with a high Gd content leads to a noteworthy improvement in the minimum vascular cross section.

Figure 6:
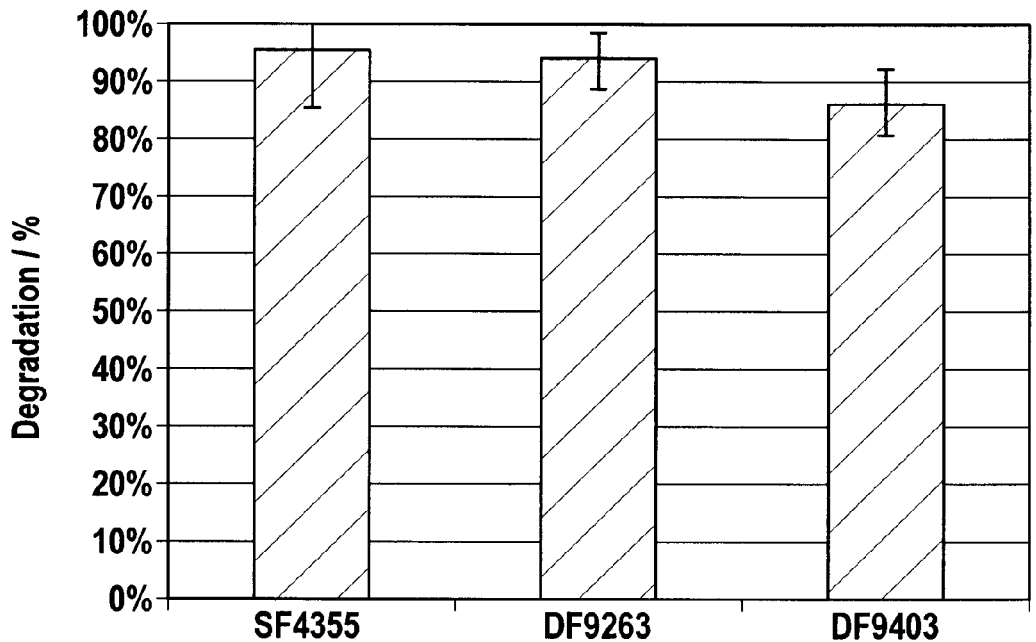
FIG. 6 shows a comparison of the extent of degradation 6 weeks after implantation with various alloy systems.

In another study, it was proven that the corrosion behavior of the inventive alloy was improved in the in-vivo test series, i.e., the corrosion was slower in comparison with traditional biocorrodible alloy systems but was not completely inhibited. FIG. 6 shows the percentage extent of degradation of alloys DF9263 and DF9403 six weeks after implantation. Stents of the allow WE43 (SF4355) were again used as reference.

Figure 7:
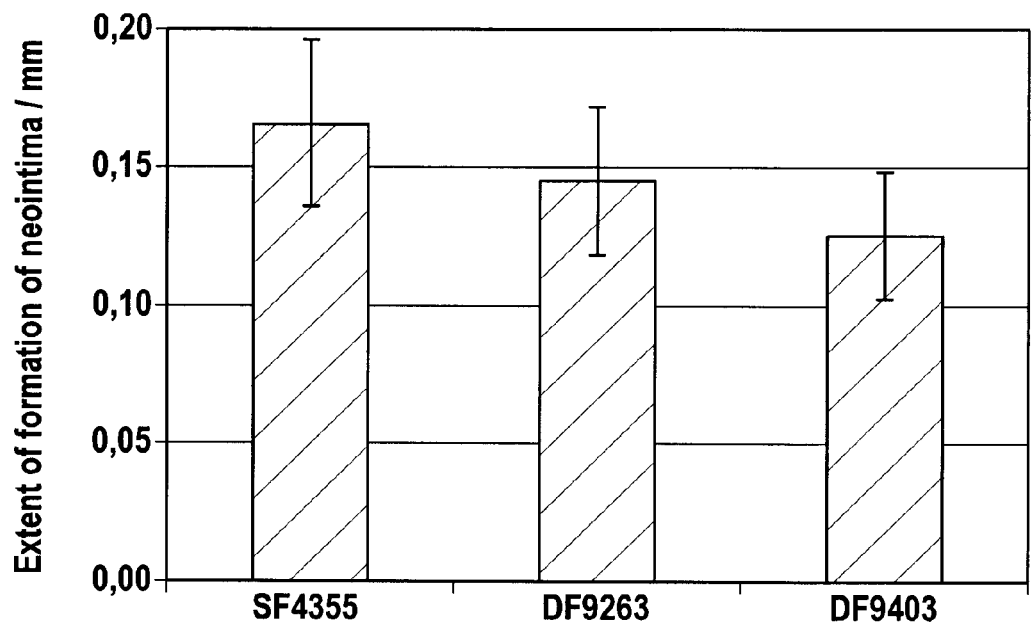
FIG. 7 shows a comparison of the development of neointima after 6 weeks with various alloy systems.

It is also especially important that the extent of formation of neointima is definitely reduced with an increase in Gd content (see FIG. 7).

Pharmaceutical Effects

In the course of biodegradation of the magnesium alloy, presumably $Gd^{3+}$ is released. The influence of this ion on the function of smooth muscle cells was therefore investigated in greater detail by determining the isotonic tonicity on porcine coronary arteries. The vascular tonicity was tested under various defined conditions (extracellular addition of $K^+$ and addition of a vasoconstrictor) while at the same time the intima was in contact with various materials. Changes in the vascular reaction after addition of $Gd^{3+}$ can definitely be interpreted on the basis of the altered sensitivity with respect to $K^+$ and the vasoconstrictive substance. Surprisingly the effect of $Gd^{3+}$ has been confirmed only in the case of the inventive alloys, in particular DF9263 but not in the case of alloys with a low Gd content. It can be concluded from these results that implantation of degradable implants based on the inventive alloy systems has positive physiological, pathological and pharmacological effects on the surrounding tissue.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implant comprising a biocorrodible magnesium alloy having the composition
   Gd: 6.0-15.0 wt %,
   Zn: 0.1-0.5% wt %,
   Zr: 0.2-0.4 wt %,
   Nd: 0-0.4 wt %,
   Y: 0.2-1.9 wt %,
   where magnesium and impurities due to the production process account for the remainder to a total of 100 wt %.

2. The implant according to claim 1, wherein the Gd content in the alloy amounts to 9 to 15.0 wt %.

3. The implant according to claim 1, wherein the Gd content in the alloy amounts to 7.1 to 13.0 wt %.

4. The implant according to claim 1, wherein the Zn content is 0.15 to 0.25 wt %.

5. The implant according to claim 1, wherein the Zr content in the alloy amounts to 0.2 to 0.3 wt %.

6. The implant according to claim 1, wherein the Nd content in the alloy amounts to 0.0 to 0.2 wt %.

7. The implant according to claim 1, wherein the Y content in the alloy amounts to 0.2 to 0.5 wt %.

8. The implant according to claim 1, wherein the implant is a stent.

9. A method for making implants, comprising the use of a biocorrodible magnesium alloy having the composition
   Gd: 6-15 wt %,
   Zn: 0.1-0.5 wt %,
   Zr: 0.2-0.4 wt %,
   Nd: 0-4.5 wt %,
   Y: 0.2-1.9 wt %,
   where magnesium as well as impurities due to the production process account for the remainder up to 100 wt %, for the production of implants.

10. A method according to claim 9, wherein the implant is a stent.

11. A method according to claim 9 wherein the biocorrodible alloy containing 6 to 15.0 wt % Gd is for restenosis prevention.

12. A method according to claim 9 wherein the biocorrodible alloy containing 6 to 15.0 wt % Gd is a vasodilating medication.

13. A stent comprising a biocorrodible magnesium alloy having the composition of between 7.1% and 13.0 wt. % Gd, between 0.1% and 0.5 wt % Zn, between 0.2% and 0.7 wt % Zr, between 2.0% and 3.0 wt % Nd, between 0.05% and 0.5 wt % Y, with the remainder of the alloy being magnesium and impurities.

14. A stent according to claim 13 wherein the biocorrodible alloy containing Gd is a vasodilating medication.

15. An implant comprising a biocorrodible magnesium alloy consisting of:
   Gd: 6.0-15.0 wt %,
   Zn: 0-0.1 wt %,
   Zr: 0.2-0.4 wt %,
   Nd: 0-0.4 wt %,
   Y: 0.2-1.9 wt %,
   where magnesium and impurities due to the production process account for the remainder to a total of 100 wt %, and wherein the implant is free of any other rare earth metals.

16. The implant according to claim 1, wherein the alloy contains from 7-13% Gd.

17. The implant according to claim 1, wherein the alloy contains from 7-8% Gd.

18. The implant according to claim 9, wherein the alloy contains from 0-0.4% Nd.

19. A stent according to claim 13, wherein the alloy contains from 7.1-8% Gd.

* * * * *